US010933075B2

(12) United States Patent
Bae et al.

(10) Patent No.: US 10,933,075 B2
(45) Date of Patent: Mar. 2, 2021

(54) MATERIALS AND METHODS FOR SUPPRESSING AND/OR TREATING BACTERIAL INFECTIONS AND RELATED SYMPTOMS

(71) Applicants: Indiana University Research and Technology Corporation, Indianapolis, IN (US); The Board Of Trustees Of The University Of Illinois, Urbana, IL (US)

(72) Inventors: Taeok Bae, Highland, IN (US); WonSik Yeo, Munster, IN (US); Hyunyoung Jeong, Oak Park, IL (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 16/054,700

(22) Filed: Aug. 3, 2018

(65) Prior Publication Data
US 2019/0038648 A1 Feb. 7, 2019

Related U.S. Application Data

(60) Provisional application No. 62/540,894, filed on Aug. 3, 2017.

(51) Int. Cl.
*A61K 31/7008* (2006.01)
*A61K 31/506* (2006.01)
*A61P 31/04* (2006.01)

(52) U.S. Cl.
CPC ........ *A61K 31/7008* (2013.01); *A61K 31/506* (2013.01); *A61P 31/04* (2018.01)

(58) Field of Classification Search
CPC .... A61K 31/7008; A61K 31/506; A61P 31/04
USPC .......................................................... 514/34
See application file for complete search history.

(56) References Cited

U.S. PATENT DOCUMENTS

2011/0150961 A1* 6/2011 Perry ................. A61K 31/74
424/411
2017/0189556 A1* 7/2017 Seleem ................. A61K 31/41

OTHER PUBLICATIONS

Glossary of medical education terms, Institute of International Medical Education. http://www.iime.org/glossary.htm Accessed in Mar. 2013. (Year: 2013).*
Boxma et al. Randomised controlled trial of single-dose antibiotic prophylaxis in surgical treatment of closed fractures: the Dutch Trauma Trial. Lancet 1996; 347: 1133-1137. (Year: 1996).*
Liu, Q., Yeo, W. S., & Bae, T. (2016). The SaeRS Two-Component System of *Staphylococcus aureus*. Genes, 7(10), 81. doi:10.3390/genes7100081.

* cited by examiner

*Primary Examiner* — Yih-Horng Shiao
(74) *Attorney, Agent, or Firm* — Faegre Drinker Biddle & Reath LLP

(57) ABSTRACT

Various aspects and embodiments disclosed herein relate generally to the modelling, treatment, reducing resistence to the treatment, prevention, and diagnosis of diseases/symptoms induced by infectious bacteria. Embodiments include methods of treating a bacterial infection, comprising the steps of: providing to a patient diagnosed with staphylococcal infection at least one therapeutically effective dose of a compound having an anti-virulence effect.

5 Claims, 11 Drawing Sheets
Specification includes a Sequence Listing.

SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Linker peptide

<400> SEQUENCE: 1

Trp Phe Asn Gly His Met Thr Leu Thr
1               5

MATERIALS AND METHODS FOR SUPPRESSING AND/OR TREATING BACTERIAL INFECTIONS AND RELATED SYMPTOMS

CROSS-REFERENCE TO RELATED APPLICATIONS

This application claims the benefit of U.S. Provisional Patent Application No. 62/540,894, filed Aug. 3, 2017, the disclosure of which is incorporated herein by reference in its entirety.

STATEMENT OF GOVERNMENTAL RIGHTS

This invention was made with government support under AI121664 awarded by the National Institutes of Health. The government has certain rights in the invention.

FIELD OF THE INVENTION

Various aspects and embodiments disclosed herein relate generally to the modelling, treatment, reducing resistence to the treatment, prevention, and diagnosis of diseases/symptoms induced by infectious bacteria.

BACKGROUND

*Staphylococcus aureus* (*S. aureus*) is a Gram-positive human pathogen colonizing skin, anterior nares and other mucosal surfaces. Approximately 30% of the human population is thought to be colonized by this bacterium. *S. aureus* causes a variety of diseases ranging from soft-tissue infections to lifethreatening diseases such as endocarditis, toxic shock syndrome, and necrotizing pneumonia. In 2005, methicillin resistant *S. aureus* (MRSA) killed more people than HIV did. In particular, *S. aureus* strain USA300 is the predominant community-associated MRSA in the USA. While the number of both hospital-acquired and community-associated infections caused by *S. aureus* has increased over the past decades, the treatment of these infections has become more difficult in part due to the emergence of multi-drug resistant strains. Therefore, development of a new class of drugs is much needed.

One drug target can include, but is not limited to, the signal transduction system SaeRS two-component system (TCS). Conserved in all clinical *S. aureus* strains, the SaeRS TCS, for example, controls production of more than 20 important virulence factors including, but not limited to, toxins (e.g., alpha-hemolysin, gamma hemolysin, and leukocidins), coagulases, adhesins, and enzymes (e.g., nucleases and proteases). Referring now to FIG. 1, the SaeRS TCS is composed of the sensor histidine kinase SaeS and the response regulator SaeR. Upon sensing a cognate signal such as human neutrophil peptides, SaeS autophosphorylates the conserved histidine residue; then the phosphoryl group is transferred to the conserved aspartic acid residue of SaeR. The phosphorylated SaeR binds to the upstream of its target genes and activates their transcription and production.

SUMMARY OF THE INVENTION

A first embodiment includes a method of treating a bacterial infection, comprising the steps of: providing to a patient at least one therapeutically effective dose of a compound according to the Formula 1:

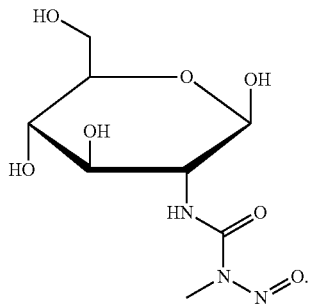

A second embodiment includes the method of the first embodiment, wherein the compound is a pharmaceutically acceptable salt of Formula 1, or a metabolite thereof.

A third embodiment includes the method according to any one of the first and the second embodiments, wherein the patent is diagnosed with a staphylococcal infection or a similar condition.

A fourth embodiment includes the method according to any one of the first to the third embodiments, wherein the bacterial infection comprises a staphylococcal infection that causes at least one symptom comprising skin infection, pneumonia, bone infection, toxic shock syndrome, blood poisoning, endocarditis, and/or a combination thereof.

A fifth embodiment includes the method according to any one of the first to the fourth embodiments, further including the step of: identifying a patent at risk for a staphylococcal infection or a similar condition.

A sixth embodiment includes the method according to any one of the first to the fifth embodiments, wherein the therapeutically effective dose of the compound according to Formula 1, is on the order of between about 5 mg to about 2000 mg and the dose of the compound is administered to the patient at least once per day. In some embodiments, the therapeutically effective dose of the compound according to Formula 1, includes, but is not limited to, on the order of between: about 10 mg to about 1900 mg; about 15 mg to about 1800 mg; about 15 mg to about 1700 mg; about 20 mg to about 1600 mg; about 25 mg to about 1500 mg; about 30 mg to about 1000 mg; about 50 mg to about 1000 mg; about 50 mg to about 800 mg; about 100 mg to about 800 mg; about 300 mg to about 800 mg; about 500 mg to about 800 mg; about 5 mg to about 50 mg; about 1000 mg to about 1700 mg; about 1200 mg to about 1700 mg; about 1500 mg to about 1700 mg; about 10 mg to about 1000 mg; about 10 mg to about 30 mg; about 1500 mg to about 2000 mg; about 100 mg to about 200 mg; about 100 mg to about 150 mg; and/or any combination thereof. Consistent with these embodiments, the therapeutically effective dose of the compound according to Formula 1, includes, but not limited to, on the order of between: about 1 mg/m$^2$ to about 1500 mg/m$^2$; about 10 mg/m$^2$ to about 1000 mg/m$^2$; about 20 mg/m$^2$ to about 800 mg/m$^2$; about 10 mg/m$^2$ to about 50 mg/m$^2$; about 800 mg/m$^2$ to about 1200 mg/m$^2$; about 50 mg/m$^2$ to about 500 mg/m$^2$; about 500 mg/m$^2$ to about 1000 mg/m$^2$; about 80 mg/m$^2$ to about 150 mg/m$^2$; about 80 mg/m$^2$ to about 120 mg/m$^2$; and/or any combination thereof.

A seventh embodiment includes a method of treating a bacterial infection, comprising the steps of: providing to a patient at least one therapeutically effective dose of a compound according to the Formula 2:

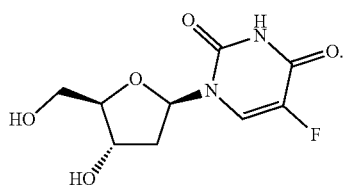 [SMILES: O=c1[nH]c(=O)n([C@H]2C[C@H](O)[C@@H](CO)O2)cc1F]

An eighth embodiment includes the method according to the method of the seventh embodiment, wherein the compound is a pharmaceutically acceptable salt of Formula 2, or a metabolite thereof.

A nineth embodiment includes the method according to any one of the seventh and the eighth embodiments, wherein the patent is diagnosed with a staphylococcal infection or a similar condition.

A tenth embodiment includes the method according to any one of the seventh to the eighth embodiments, wherein the bacterial infection comprises a staphylococcal infection that causes at least one symptom comprising skin infection, pneumonia, bone infection, toxic shock syndrome, blood poisoning, endocarditis, and/or a combination thereof.

An eleventh embodiment includes the method according to any one of the seventh to the nineth embodiments, further including the step of: identifying a patent at risk for a staphylococcal infection or a similar condition.

A twelfth embodiment includes the method according to any one of the seventh to the tenth embodiments, wherein the therapeutically effective dose of the compound according to Formula 2, is on the order of between about 0.01 mg to about 200 mg and the dose of the compound is administered to the patient at least once per day. In some embodiments, the therapeutically effective dose of the compound according to Formula 2, includes, but is not limited to, on the order of between: about 0.01 mg to about 150 mg; about 0.01 mg to about 100 mg; about 0.01 mg to about 80 mg; about 0.01 mg to about 60 mg; about 0.05 mg to about 100 mg; about 0.05 mg to about 80 mg; about 0.05 mg to about 50 mg; about 0.1 mg to about 100 mg; about 0.1 mg to about 50 mg; about 0.2 mg to about 100 mg; about 0.2 mg to about 50 mg; about 0.5 mg to about 100 mg; about 0.5 mg to about 50 mg; about 100 mg to about 200 mg; about 100 mg to about 150 mg; and/or any combination thereof. Consistent with these embodiments, the therapeutically effective dose of the compound according to Formula 2, includes, but not limited to, on the order of between: about 0.01 mg/m$^2$ to about 100 mg/m$^2$; about 0.01 mg/m$^2$ to about 80 mg/m$^2$; about 0.01 mg/m$^2$ to about 50 mg/m$^2$; about 0.01 mg/m$^2$ to about 25 mg/m$^2$; about 0.05 mg/m$^2$ to about 100 mg/m$^2$; about 0.05 mg/m$^2$ to about 80 mg/m$^2$; about 0.05 mg/m$^2$ to about 50 mg/m$^2$; about 80 mg/m$^2$ to about 150 mg/m$^2$; about 80 mg/m$^2$ to about 120 mg/m$^2$; and/or any combination thereof.

A thirteenth embodiment includes a method of treating a bacterial infection, comprising the steps of: providing to a patient at least one therapeutically effective dose of a compound according to the Formula 3:

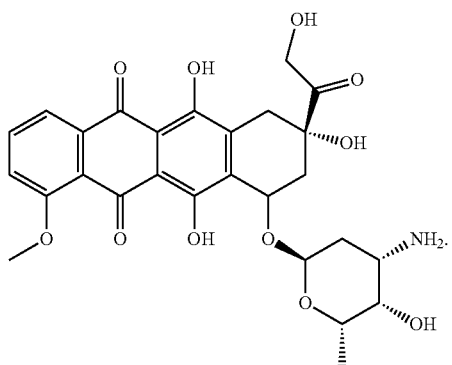

A fourteenth embodiment includes the method according to the thirteenth embodiment, wherein the compound is a pharmaceutically acceptable salt of Formula 3, or a metabolite thereof.

A fifteenth embodiment includes the method according to any one of the thirteenth and the fourteenth embodiments, wherein the patent is diagnosed with a staphylococcal infection or a similar condition.

A sixteenth embodiment includes the method according to any one of the thirteenth to the fifteenth embodiments, wherein the bacterial infection comprises a staphylococcal infection that causes at least one symptom comprising skin infection, pneumonia, bone infection, toxic shock syndrome, blood poisoning, endocarditis, and a combination thereof.

A seventeenth embodiment includes the method according to any one of the thirteenth to the sixteenth embodiments, further including the step of: identifying a patent at risk for a staphylococcal infection or a similar condition.

An eighteenth embodiment includes the method according to any one of the thirteenth to the seventeenth embodiments, wherein the therapeutically effective dose of the compound according to Formula 3, is on the order of between about 10 mg to about 2000 mg and the dose of the compound is administered to the patient at least once per day. In some embodiments, the therapeutically effective dose of the compound according to Formula 3, includes, but is not limited to, on the order of between: about 10 mg to about 1900 mg; about 15 mg to about 1800 mg; about 15 mg to about 1700 mg; about 20 mg to about 1600 mg; about 25 mg to about 1500 mg; about 30 mg to about 1000 mg; about 50 mg to about 1000 mg; about 50 mg to about 800 mg; about 100 mg to about 800 mg; about 300 mg to about 800 mg; about 500 mg to about 800 mg; about 5 mg to about 50 mg; about 1000 mg to about 1700 mg; about 1200 mg to about 1700 mg; about 1500 mg to about 1700 mg; about 10 mg to about 1000 mg; about 10 mg to about 30 mg; about 1500 mg to about 2000 mg; about 100 mg to about 200 mg; about 100 mg to about 150 mg; and/or any combination thereof. Consistent with these embodiments, the therapeutically effective dose of the compound according to Formula 3, includes, but not limited to, on the order of between: about 1 mg/m$^2$ to about 1500 mg/m$^2$; about 10 mg/m$^2$ to about 1000 mg/m$^2$; about 20 mg/m$^2$ to about 800 mg/m$^2$; about 10 mg/m$^2$ to about 50 mg/m$^2$; about 800 mg/m$^2$ to about 1200 mg/m$^2$; about 50 mg/m$^2$ to about 500 mg/m$^2$; about 500 mg/m$^2$ to about 1000 mg/m$^2$; about 80 mg/m$^2$ to about 150 mg/m$^2$; about 80 mg/m$^2$ to about 120 mg/m$^2$; and/or any combination thereof.

A nineteenth embodiment includes a method of reducing resistance to an antibiotic therapeutic, comprising the steps of: treating a patient at least one therapeutically effective dose of at least one compound comprising:

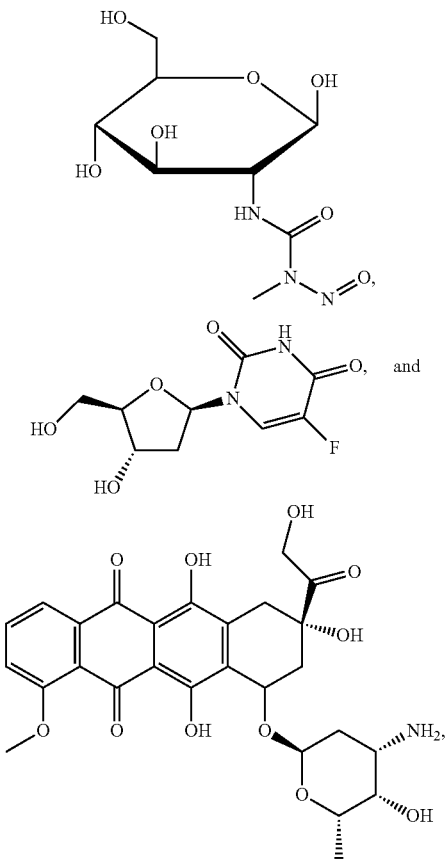

or a pharmaceutically acceptable salt thereof, or a metabolite thereof.

A twentieth embodiment includes a method of reducing or inhibiting the activity of at least one agent involved in a SaeRS two-component system, comprising the steps of: providing a subject at least one therapeutically effective dose of at least one compound comprising:

or a pharmaceutically acceptable salt thereof, or a metabolite thereof.

A twenty first embodiment includes the method according to the twentieth embodiment, wherein the at least one agent comprises SaeS, SaeR, and/or a part or a fragment thereof.

A twenty second embodiment includes the method according to any one of the twentieth and the twenty first embodiments, wherein the subject comprises a human, an animal, a cell, and/or a tissue.

BRIEF DESCRIPTION OF SEQUENCES

SEQ ID NO:1. WFNGHMTLT

DESCRIPTION

Figure 1:
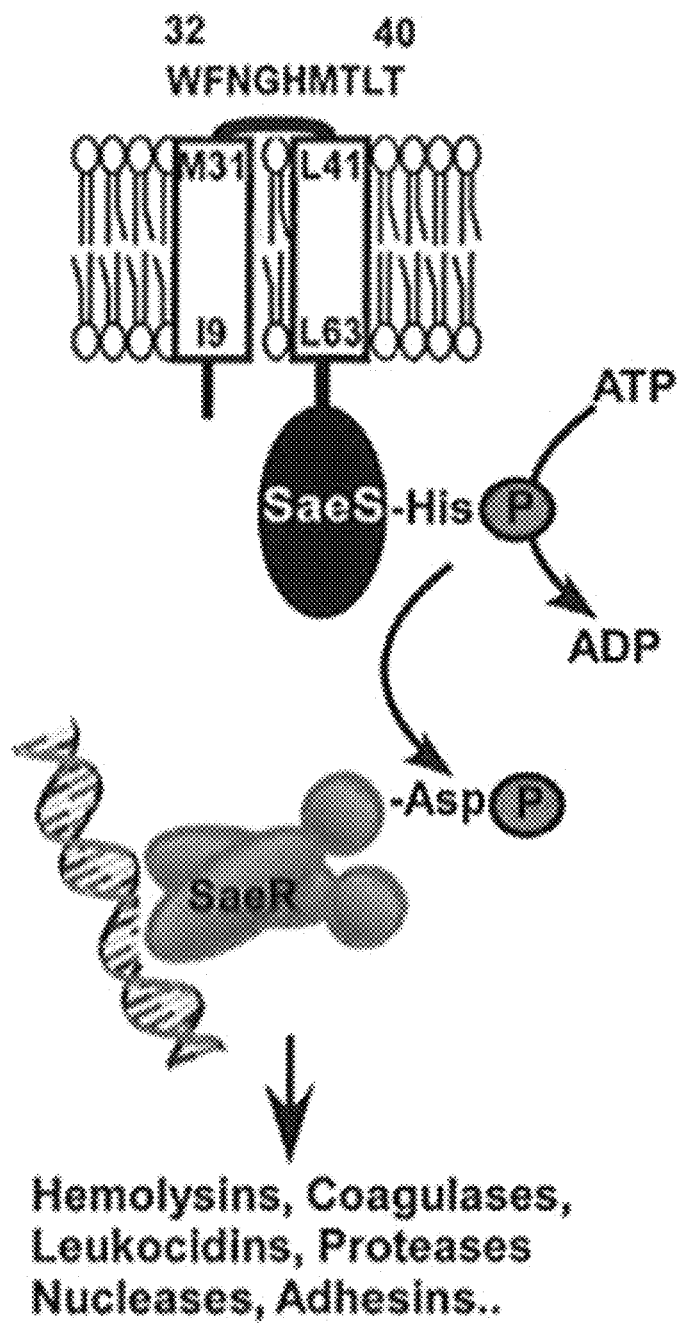
FIG. 1. Schematic diagram illustrating a process of controlling virulence factor production by SaeRS TCS.

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of this disclosure and the claims.

As used herein, unless explicitly stated otherwise or clearly implied otherwise the term 'about' refers to a range of values plus or minus 10 percent, e.g. about 1.0 encompasses values from 0.9 to 1.1.

The term, "treating" as used herein unless stated or implied otherwise, includes administering to a human or an animal patient at least one dose of a compound, treating includes preventing or lessening the likelihood and/or severity of at least one disease as well as limiting the length of an illness or the severity of an illness, treating may or may not result in a cure of the disease.

As used herein, unless explicitly stated otherwise or clearly implied otherwise the terms 'therapeutically effective dose,' 'therapeutically effective amounts,' and the like, refer to a portion of a compound that has a net positive effect on health and well being of a human or other animal. Therapeutic effects may include an improvement in longevity, quality of life and the like these effects also may also include a reduced susceptibility to developing disease or deteriorating health or well being. The effects may be immediate realized after a single dose and/or treatment or they may be cumulative realized after a series of doses and/or treatments. A "therapeutically effective amount" in general means the amount that, when administered to a subject or animal for treating a disease, is sufficient to affect the desired degree of treatment for the disease.

As used herein, "inhibition" or "inhibitory activity" each encompass whole or partial reduction of activity or effect of an enzyme or all and/or part of a pathway that includes an enzyme that is effected either directly or indirectly by the inhibitor or a pathway that is effected either directly or indirectly by the activity of the enzyme which is effected either directly or indirectly by the inhibitor.

As used herein, the term "pharmaceutically acceptable salt" is defined as a salt wherein the desired biological activity of the inhibitor is maintained and which exhibits a minimum of undesired toxicological effects. Non-limiting examples of such a salt are (a) acid addition salts formed with inorganic acids (e.g., hydrochloric acid, hydrobromic acid, sulphuric acid, phosphoric acid, nitric acid, and the like), and salts formed with organic acids (such as e.g. acetic acid, oxalic acid, tartaric acid, succinic acid, malic acid, ascorbic acid, benzoic acid, tannic acid, palmitic acid, polyglutamic acid, naphthalene sulphonic acid, naphthalene disulphonic acid, polygalacturonic acid and the like); (b) base additional salts formed with metal cations such as zinc, calcium, bismuth, barium, magnesium, aluminum, copper, cobalt, nickel, cadmium, sodium, potassium and the like, or with a cation formed from ammonia, N,N-dibenzylethylenediamine, D-glucosamine, tetraethylammonium or ethylenediamine; or (c) combinations of (a) and (b); e.g. a zinc tannate or the like.

Pharmaceutically acceptable salts include salts of compounds of the invention that are safe and effective for use in mammals and that possess a desired therapeutic activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention may form pharmaceutically acceptable salts with various amino acids. Suitable base salts include, but are not limited to, aluminum, calcium, lithium, magnesium, potassium, sodium, zinc, and diethanolamine salts. For additional information on some pharmaceutically acceptable salts that can be used to practice the invention please reviews such as Berge, et al., 66 J. PHARM. SCI. 1-19 (1977), Haynes, et al, J. Pharma. Sci., Vol. 94, No. 10, October 2005, pgs. 2111-2120 and See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977.

Pharmaceutical formulation: The compounds of the invention and their salts may be formulated as pharmaceutical compositions for administration. Such pharmaceutical compositions and processes for making the same are known in the art for both humans and non-human mammals. See, e.g., REMINGTON: THE SCIENCE AND PRACTICE OF PHARMACY, (A. Gennaro, et al., eds., 19$^{th}$ ed., Mack Publishing Co., 1995). Formulations can be administered through various means, including oral administration, parenteral administration such as injection (intramuscular, subcutaneous, intravenous, intraperitoneal) or the like; transdermal administration such as dipping, spray, bathing, washing, pouring-on and spotting-on, and dusting, or the like. Additional active ingredients may be included in the formulation containing a compound of the invention or a salt thereof.

The pharmaceutical formulations of the present invention include those suitable for oral, parenteral (including subcutaneous, intradermal, intramuscular and intravenous) and rectal administration. The formulations may be presented in unit dosage form and may be prepared by any of the methods well known in the art of pharmacy. All methods include the step of bringing into association the active ingredient, i.e., the compound or salt of the present invention, with the carrier. In general, the formulations are prepared by uniformly and intimately bringing into association the active ingredient with a liquid carrier or, a finely divided solid carrier or both, and then, if necessary, forming the associated mixture into the desired formulation.

The pharmaceutical formulations of the present invention suitable for oral administration may be presented as discrete units, such as a capsule, cachet, tablet, or lozenge, each containing a predetermined amount of the active ingredient; as a powder or granules; as a solution or a suspension in an aqueous liquid or non-aqueous liquid such as a syrup, elixir or a draught, or as an oil-in-water liquid emulsion or a water-in-oil liquid emulsion. The formulation may also be a bolus, electuary or paste.

The pharmaceutical formulations of the present invention suitable for parenteral administration include aqueous and non-aqueous sterile injection solutions, and may also include an antioxidant, buffer, a bacteriostat and a solution which renders the composition isotonic with the blood of the recipient, and aqueous and non-aqueous sterile suspensions which may contain, for example, a suspending agent and a thickening agent. The formulations may be presented in a single unit-dose or multi-dose containers, and may be stored in a lyophilized condition requiring the addition of a sterile liquid carrier prior to use.

Pharmaceutically acceptable carrier: Pharmaceutically acceptable carrier, unless stated or implied otherwise, is used herein to describe any ingredient other than the active component(s) that maybe included in a formulation. The choice of carrier will to a large extent depend on factors such as the particular mode of administration, the effect of the carrier on solubility and stability, and the nature of the dosage form.

A tablet may be made by compressing or moulding the active ingredient with the pharmaceutically acceptable carrier. Compressed tablets may be prepared by compressing in a suitable machine the active ingredient in a free-flowing form, such as a powder or granules, in admixture with, for example, a binding agent, an inert diluent, a lubricating agent, a disintegrating and/or a surface active agent. Moulded tablets may be prepared by moulding in a suitable machine a mixture of the powdered active ingredient moistened with an inert liquid diluent. The tablets may optionally be coated or scored and may be formulated so as to provide slow or controlled release of the active ingredient.

As used herein, "infectious bacteria" include, but are not limited to, *streptococcus, staphylococcus, listeria, salmonella*, and *E. coli*.

*Staphylococcus aureus* (*S. aureus*) is a Gram-positive human pathogen colonizing skin, anterior nares and other mucosal surfaces. Approximately 30% of the human population is thought to be colonized by this bacterium. *S. aureus* causes a variety of diseases ranging from soft-tissue infections to lifethreatening diseases such as endocarditis, toxic shock syndrome, and necrotizing pneumonia. In 2005, methicillin resistant *S. aureus* (MRSA) killed more people than HIV did. In particular, *S. aureus* strain USA300 is the predominant community-associated MRSA in the USA. Oxacillin is a penicillinase-resistant β-lactam. It is similar to methicillin, and has replaced at least in part methicillin in clinical use. Since it is resistant to penicillinase enzymes, such as that produced by *Staphylococcus aureus*, it is widely used clinically in the US to treat penicillin-resistant *Staphylococcus aureus*. However, with the introduction and widespread use of both oxacillin and methicillin, antibiotic-resistant strains called methicillin-resistant and oxacillin-resistant *Staphylococcus aureus* (MRSA/ORSA) have become increasingly prevalent worldwide. In part due to the emergence of multi-drug resistant strains, development of a new class of drugs is much needed.

The Gram-positive pathogen *Staphylococcus aureus* is a major cause of morbidity and mortality. This bacterium causes a variety of diseases ranging from soft-tissue infections to life-threatening invasive diseases such as endocarditis, toxic shock syndrome, and necrotizing pneumonia. The success of *S. aureus* as a human pathogen is largely due to its production of multiple virulence factors, which contribute to various aspects of the bacterial pathogenesis from binding to host tissues to immune evasion. In *S. aureus*, the production of virulence factors is controlled by an intricate network of transcription regulators including alternative sigma factor $\sigma^B$, DNA binding proteins (e.g., SarA and its homologues) and two-component signaling systems (e.g., AgrAC, Ar1RS, SrrAB, and SaeRS). The SaeRS two-component system (TCS) plays a major role in controlling the production of over 20 virulence factors including hemolysins, leukocidins, superantigens, surface proteins, and proteases.

The sae (*S. aureus* exoprotein expression) locus, which encodes the SaeRS TCS, was identified by Giraudo et al. in 1994 during their characterization of a Tn551 mutant for its defect in the production of exoproteins (e.g., α-hemolysin, β-hemolysin, nuclease, and coagulase). As with other typical TCSs, the signaling cascade in the SaeRS TCS starts when SaeS, the sensor histidine kinase, detects cognate environmental signals (e.g., human neutrophil peptides, HNPs) and autophosphorylates at the conserved His131 residue. The phosphoryl group is then transferred to Asp51 of SaeR, and the phosphorylated SaeR (SaeR-P) binds to SaeR binding sequence (SBS) and, in most cases, activates the transcription of the target genes. (FIG. 1). See e.g., Liu Q, Yeo W-S, Bae T. *The SaeRS Two-Component System of Staphylococcus aureus*. GENES. 2016; 7(10):81.

Figure 2A:
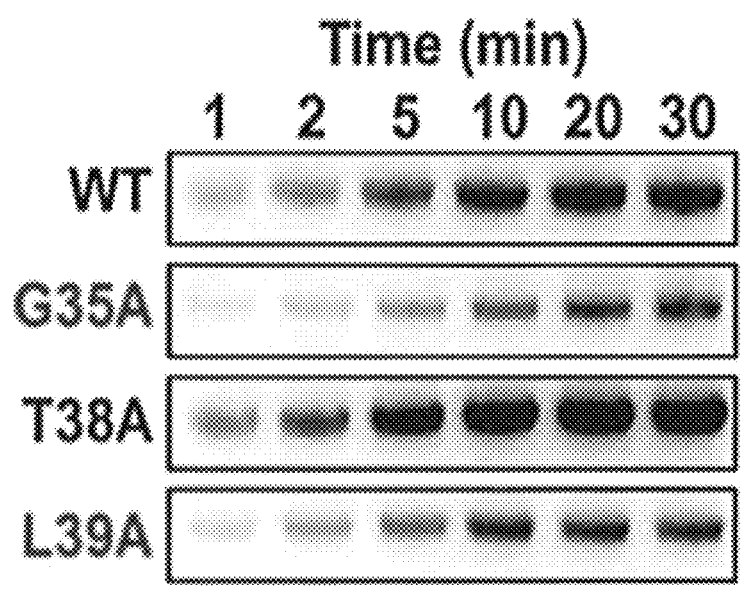
FIG. 2A. Western blot analysis of autophosphorylation. Purified MBP-SaeS proteins were incubated with [y-$^{32}$P]-ATP at room temperature for 30 min. At the time points indicated, the level of phosphorylated SaeS was analyzed by SDS-PAGE and phosphorimager analysis.
Figure 2B:
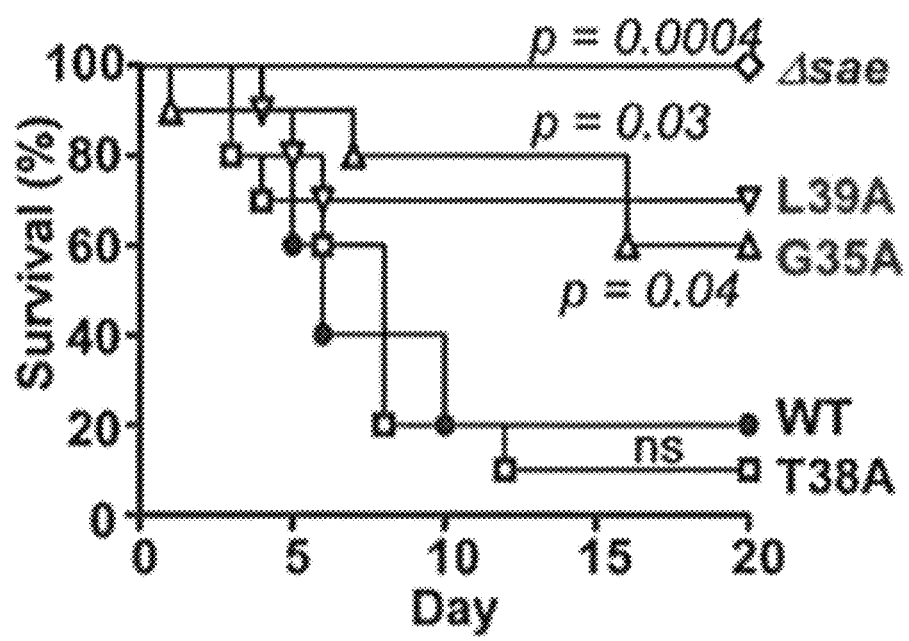
FIG. 2B. Graph illustrating the effect on survival. Mice were infected with the test S. aureus strains via retro-orbital injection and watched for 20 days. WT, wild type; G35A, SaeS with G35A mutation; T38A, SaeS with T38A mutation; L39A, SaeS with L39A mutation; Δsae, deletion of the saeRS genes; ns, not significant.

SaeS is composed of 351 amino acids (a.a.) where His131 is the phosphorylation site. As a sensor histidine kinase, its kinase activity determines the level of SaeR-P, the effector molecule of the SaeRS TCS. Unlike most other sensor histidine kinases, the sensor kinase SaeS does not have a ligand binding domain between two transmembrane helices. Instead, it has a 9 a.a.-linker peptide (WFNGHMTLT (SEQ ID NO:1) in FIG. 1). Referring now to FIG. 2A, alanine substitution at G35 or L39 reduced the autokinase activity of SaeS (G35A, and L39A). *S. aureus* strains carrying those mutant alleles also exhibited lower virulence in the murine model of blood infection (FIG. 2B), demonstrating that SaeS is a viable target for development of an antivirulence drug against staphylococcal infections. Indeed, complete shutdown of the SaeRS TCS by deletion mutagenesis abolishes the staphylococcal virulence (Asae in FIG. 2B).

The Reporter System for Sae-Inhibitor Screening

The sae operon consists of four genes (saeP, saeQ, saeR, and saeS), and the two promoters P1 and P3. The P1 promoter resides in the front of the very first gene saeP and can transcribe all four genes. The P1 promoter has two SaeR binding sequences (SBSs). The P1 promoter in front of the sae operon is well characterized target of the SaeRS two component system. Here, the reporter plasmid pYJ-P1-GFP was used in the library screening and the expression level of GFP was interpreted as the Sae activity.

Small Compound Library Screening with pYJ-P1-GFP

In the library screening, *S. aureus* strain USA300 was grown with pYJ-P1-GFP in the presence of 10 µM test compound for 3 hours. Then the effects of the each drug on growth and GFP expression were measured. In the primary screening, about 9,000 test compounds (3,000 FDA-approved drugs, 6,000 DCL library compounds) were tested. From the screening, 85 (59 FDA approved drugs and 26 DCL library compounds) compounds exhibited significant inhibition of the activity of P1 promoter with minimal effects on bacterial growth.

Murine Model of Peritoneal Infection

The identified 85 compounds from the initial screening were further tested for their anti-virulence effect in a murine model of peritoneal infection. In this model, mice were i.p. infected with *S. aureus* USA300. One hour post infection, the test compounds were administered via i.p. injection once every day for 7 days. As a result, at least 7 (6 FDA-approved drugs and 1 ChemBridge DIVERSet-CL (DCL) compound) compounds showed promising anti-virulence effect. For example, Erythrosine sodium, Fluvastatin, Pregnenolone succinate, Streptozotocin, Floxuridine, Doxorubicin, and DCL_25962176 exhibited anti-virulence effect; 50 µg of each compound was administered via i.p. injection.

Animal Experiment for Confirmation

The selected compounds were further examined for their anti-virulence effect by repeating the mouse experiment. From these experiments, at least three compounds (e.g., Streptozotocin, Floxuridine, and Doxorubicin) exhibited significant anti-virulence effect.

Figure 3A:
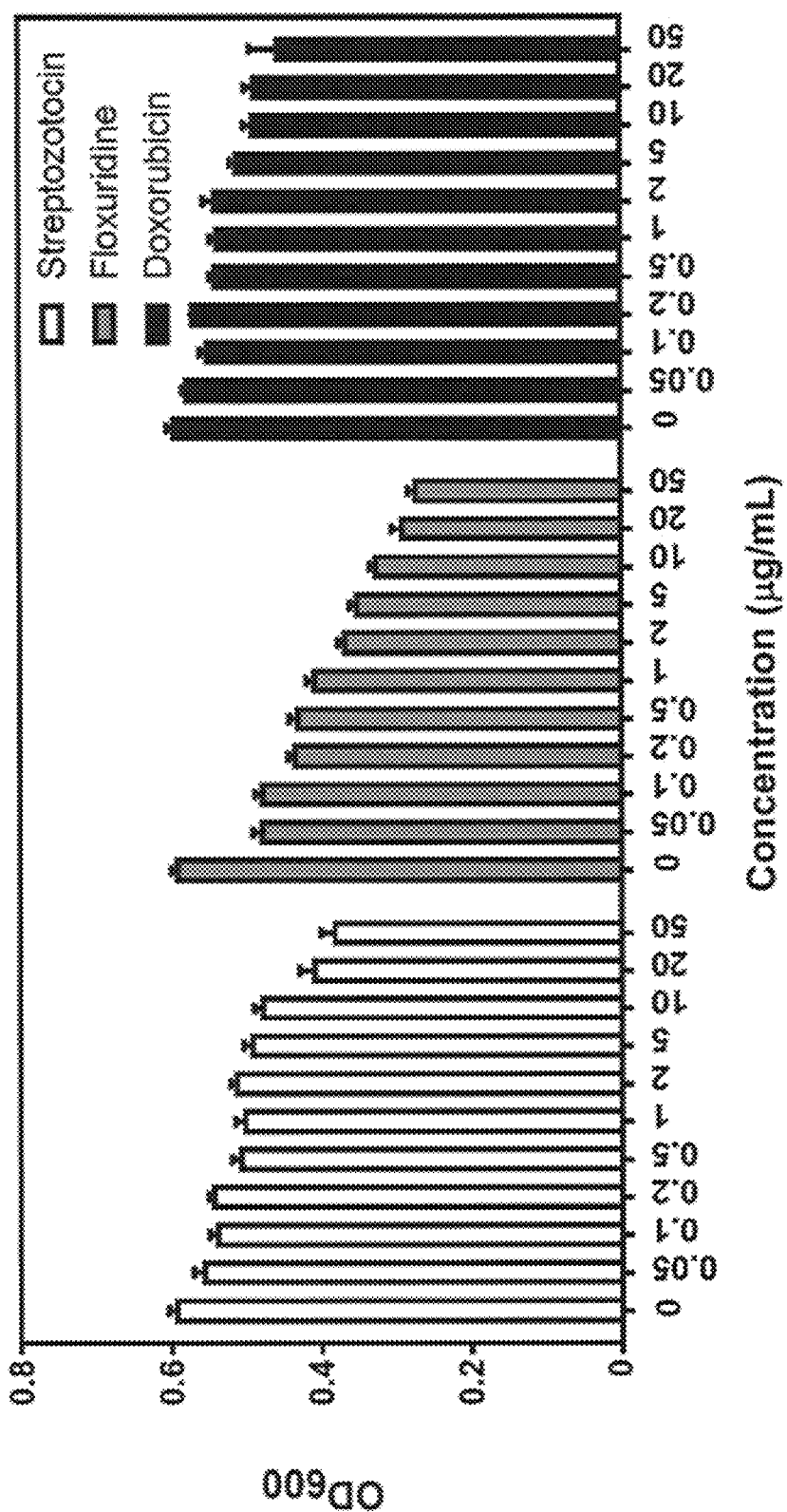
FIG. 3A. Graph illustrating the effect of three compounds on growth of Staphylococcus aureus. Cells were grown in TSB for 3 hours in the presence of the compounds (e.g., Streptozotocin, Floxuridine, and Doxorubicin) using various concentrations as indicated.
Figure 3B:
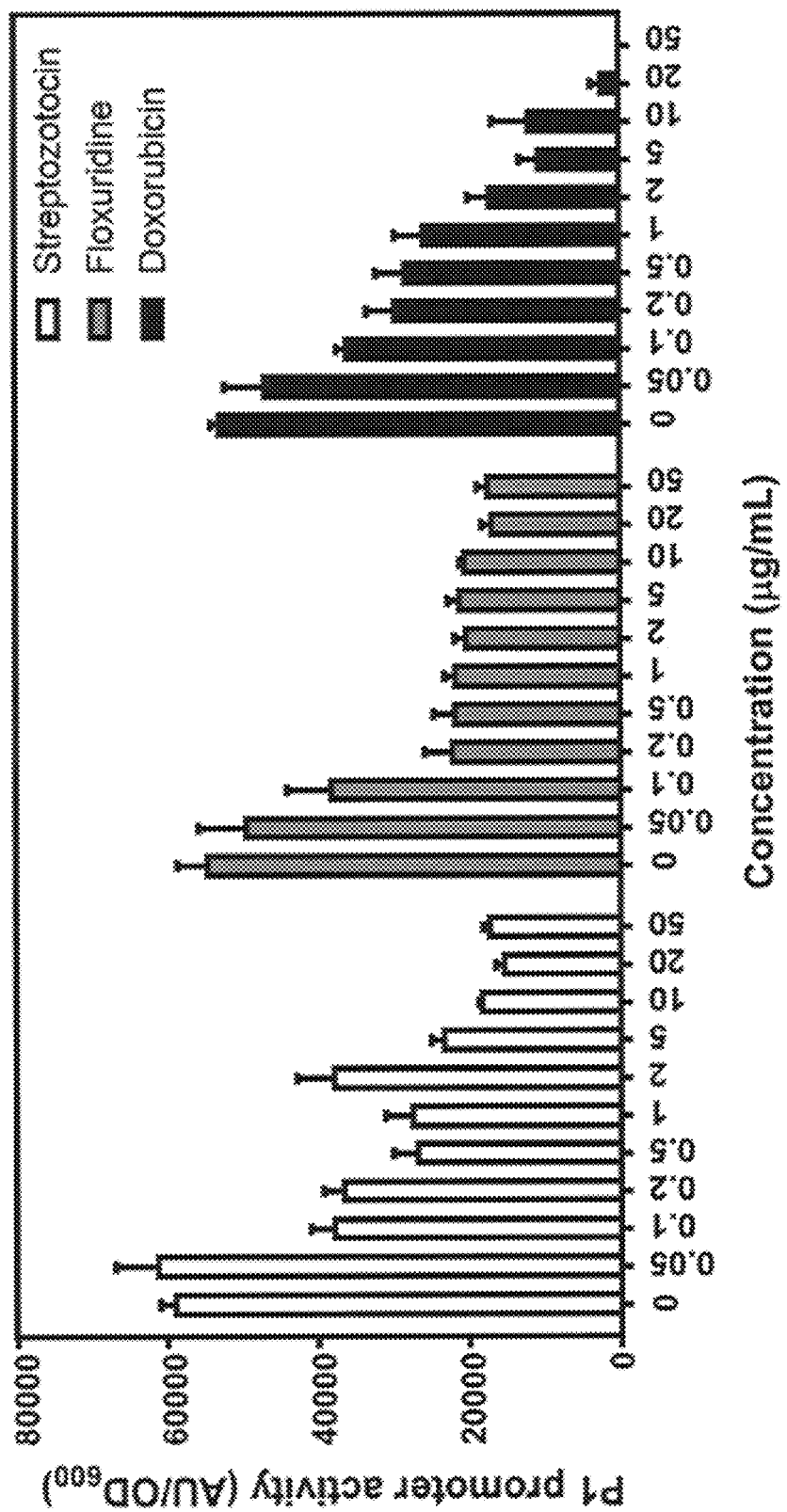
FIG. 3B. Graph illustrating the effect of three compounds on Sae activity of Staphylococcus aureus. Cells were grown in TSB for 3 hours in the presence of the compounds (e.g., Streptozotocin, Floxuridine, and Doxorubicin) using various concentrations as indicated. The P1 promoter has two SaeR binding sites and its activity is an excellent indicator for the Sae activity.

Referring now to FIGS. 3A and 3B, the effects of the three compounds on growth (A) and Sae activity (B) of *Staphylococcus aureus* were measured. The cells were grown in TSB for 3 h in the presence of the compounds with various concentrations as indicated. Cells were treated with the three compounds (e.g., Streptozotocin, Floxuridine, and Doxorubicin) and all exhibited reduced growth and reduced P1 promoter activity.

Figure 4:
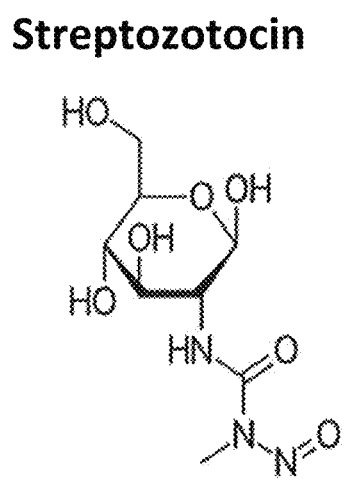
FIG. 4. Effect of Streptozotocin on survival. Steptozotocin exhibits anti-virulence activity against S. aureus infection in mice. Open circles represent percent survival of treated mice (i.e., steptozotocin) after the indicated period. Closed circles represent percent survival of untreated mice (i.e., control). S. aureus (2×10$^8$ CFU) were i.p. injected into mice (n=10-18).
Figure 4:
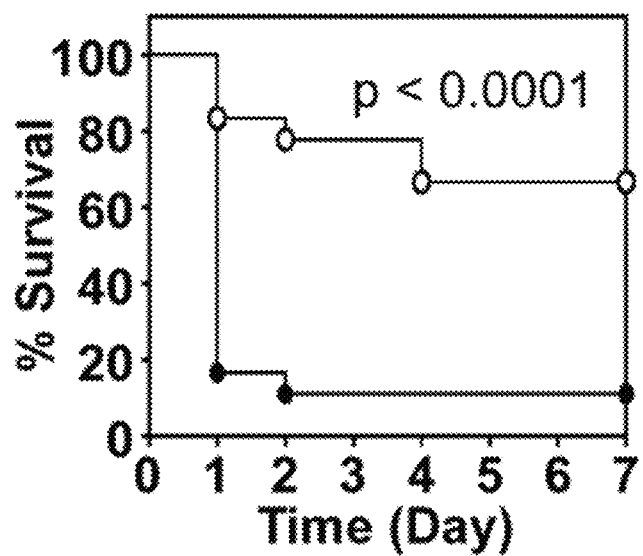
Figure 5:
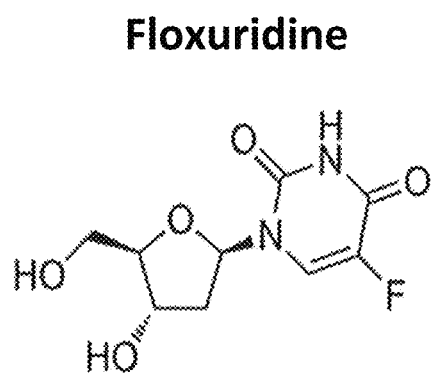
FIG. 5. Effect of Floxuridine on survival. Floxuridine exhibits anti-virulence activity against S. aureus infection in mice. Open circles represent percent survival of treated mice (i.e., floxuridine) after the indicated period. Closed circles represent percent survival of untreated mice (i.e., control). *S. aureus* ($2\times10^8$ CFU) were i.p. injected into mice (n=10-18).
Figure 5:
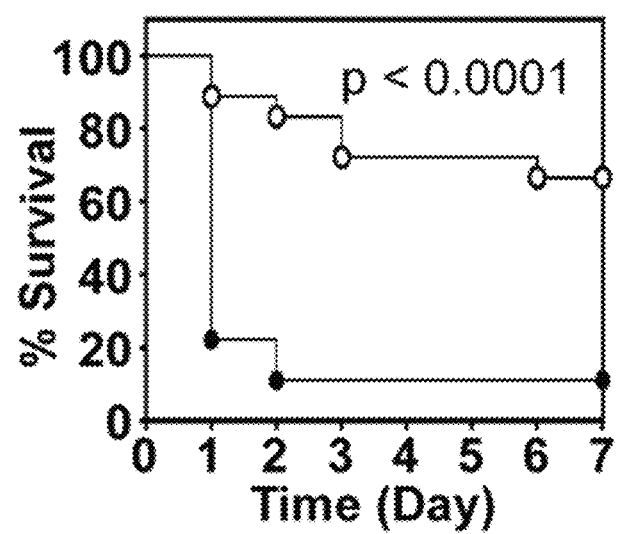
Figure 6:
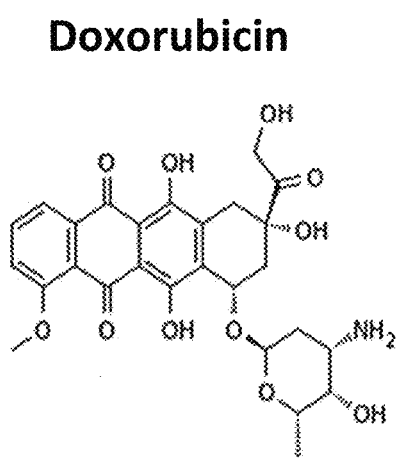
FIG. 6. Effect of Doxorubicin on survival. Doxorubicin exhibits anti-virulence activity against *S. aureus* infection in mice. Open circles represent percent survival of treated mice (i.e., doxorubicin) after the indicated period. Closed circles represent percent survival of untreated mice (i.e., control). *S. aureus* ($2\times10^8$ CFU) were i.p. injected into mice (n=10-18).
Figure 6:
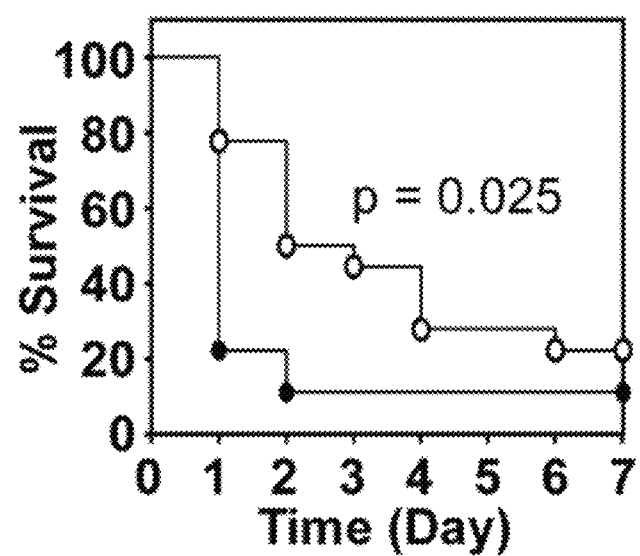

Referring now to FIG. 4, steptozotocin exhibited anti-virulence activity against *S. aureus* infection in mice. Referring now to FIG. 5, floxuridine exhibited anti-virulence activity against *S. aureus* infection in mice. Referring now to FIG. 6, doxorubicin exhibited anti-virulence activity against *S. aureus* infection in mice.

Figure 7:
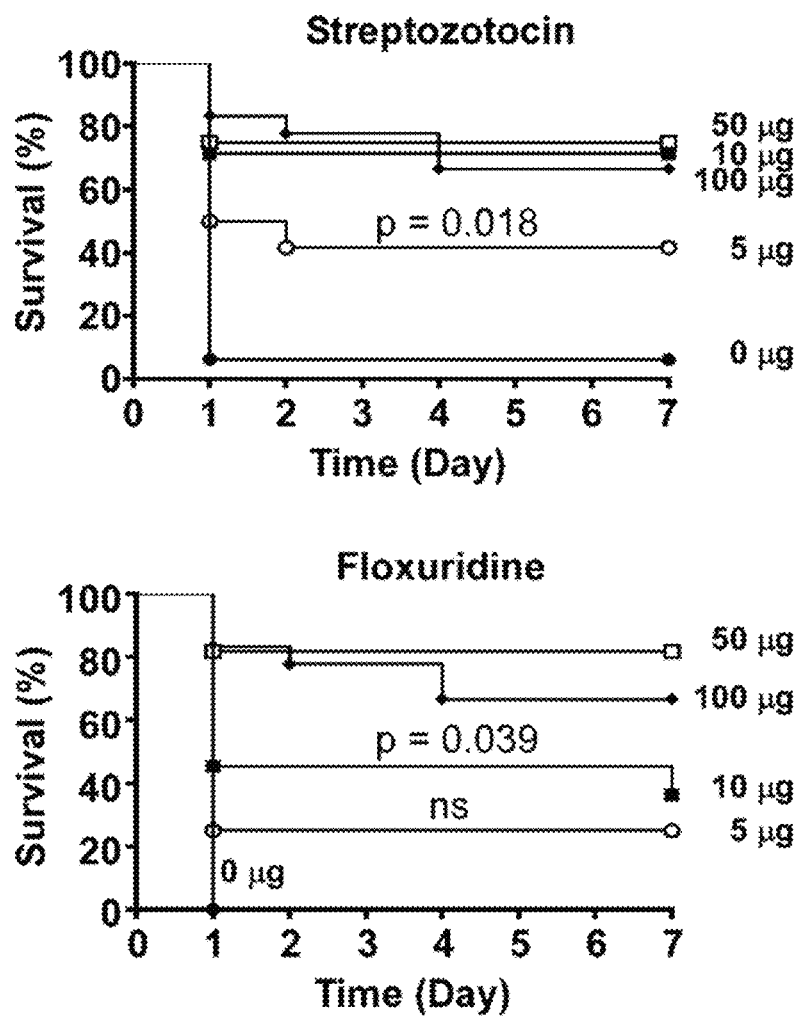
FIG. 7. Dose-dependent efficacy of streptozotocin and floxuridine. (ns, not significant)

Streptozotocin and floxuridine, for example, showed very promising in vivo efficacy. To determine the minimal dosage of the compounds for their protective effect, a different amount of the compounds (0-100 µg) were administered after *S. aureus* infection for 7 days as described above. Referring now to FIG. 7, a comparable in vivo efficacy was observed for 10-100 µg of streptozoton. Although lower, even 5 µg of streptozotocin showed statistically significant in vivo efficacy. In case of floxuridine, the administration of 50 µg and 100 µg showed similar in vivo efficacy. Although lower, 10 µg of floxuridine showed statistically significant in vivo efficacy against *S. aureus* infection.

Figure 8:
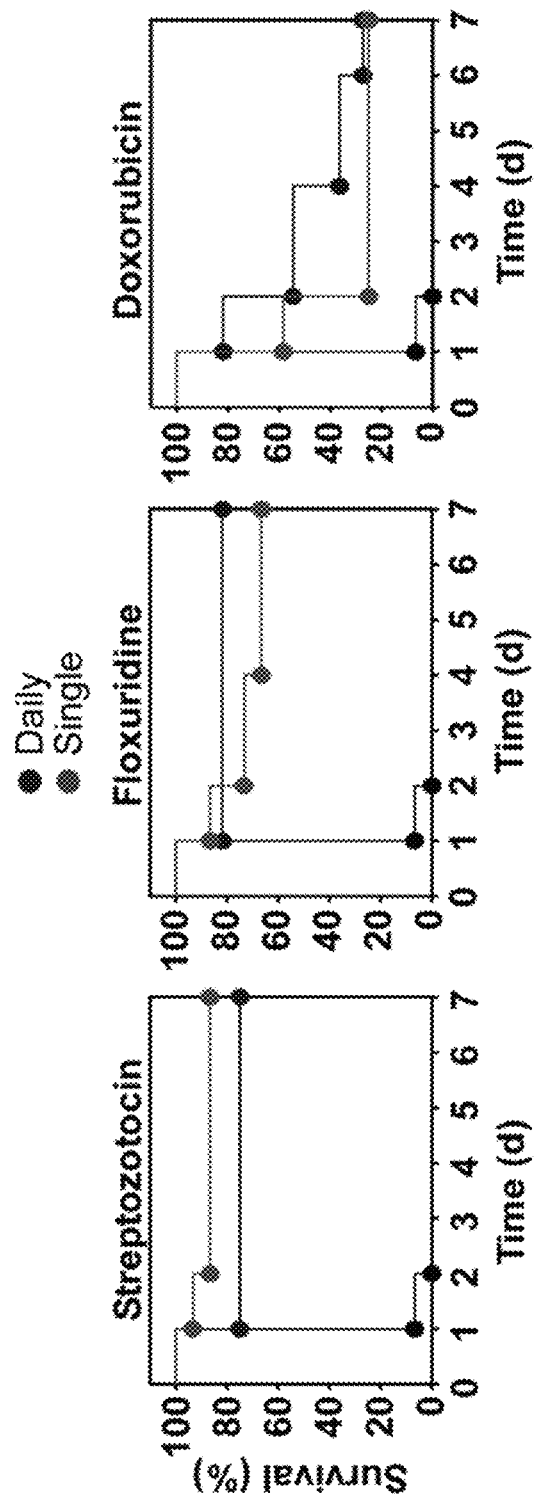
FIG. 8. Effect of single administration of the compounds on murine survival. Fifteen mice were used for streptozotocin and floxuridine while ten mice were used for doxorubicin. For comparison purposes, the daily administration results were superimposed.

The biological half-life of streptozotocin is about 35-40 min. Floxuridine is also rapidly catabolized to 5'fluorouracil (5-FU). The half-life of 5-FU is also known to be about 8-14 minutes. Although we administered the compounds every day for 7 days, due to their short half-lives, it is likely that *S. aureus* cells were exposed to the compounds only briefly. Therefore, it is possible that a brief exposure to the compounds might cause a permanent anti-virulence effect on the bacteria. To examine the hypothesis, after 2 h post infection with *S. aureus*, we administered the compounds only once (25 µg for streptozotocin and floxuridine; 50 µg for doxorubicin) and watched the infected mice for 7 days. Referring now to FIG. 8, the single administration of the compounds showed a similar protective effect to daily administration.

Figure 9:
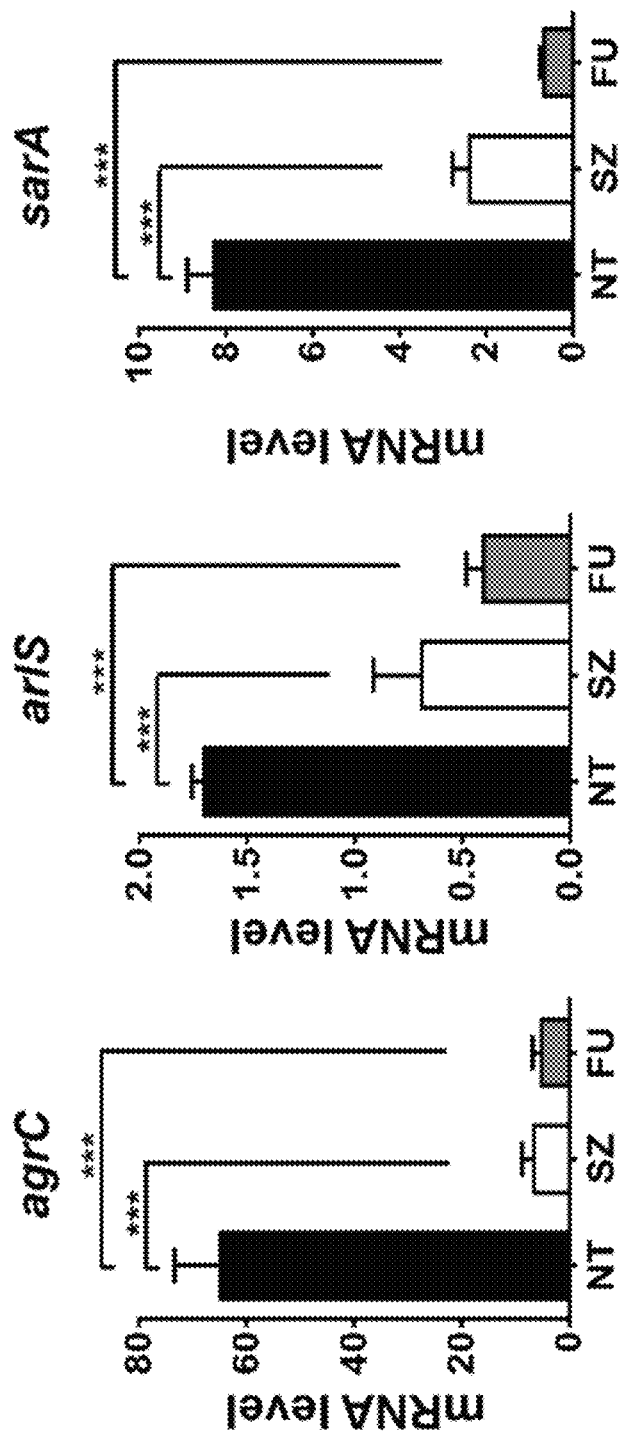
FIG. 9. Streptozotocin (SZ) and floxuridine (FU) repress other signalling systems critical for staphylococcal virulence. The transcription level of the indicated genes was analyzed by qRT-PCR and normalized by the transcription level of gyrB. agrC, the gene of the sensor kinase of the Agr quorum sensing system; arlS, the gene of the sensor kinase of the Arl two componenet system; sarA, the gene of the DNA binding protein SarA; NT, no treatment.

The virulence of *S. aureus* is thought to be controlled by multiple signaling systems. Along with the Sae signaling system, the Agr quorum sensing system, Arl two-component system, and SarA DNA binding protein are known to contribute to staphylococcal virulence. To explain the high in vivo efficacy of streptozotocin and floxuridine, *S. aureus* USA300 was treated with 1 µg/mL (=3.8 µM for streptozotocin, 4 µM for floxuridine) for 3 h, purified total RNA and carried out qRT-PCR. Referring now to FIG. 9, streptozotocin and floxuridine inhibit multiple signaling systems critical for staphylococcal virulence.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety to the extent they are not inconsistent with the explicit teachings of this specification.

We claim:

1. A method of lessening the severity of Staphylococcal infection in a patient in need thereof, consisting of:

administering to the patient an active ingredient consisting of a single therapeutically effective dose of an agent, wherein the agent is the compound according to the Formula 2:

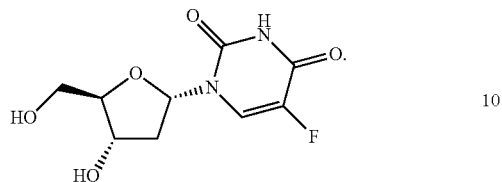

or a pharmaceutically acceptable salt or a metabolite thereof, and wherein the therapeutically effective dose is between about 0.01 mg to about 100 mg; and optionally identifying the patient colonized by a staphylococcus before the administering step.

2. The method of claim 1, wherein the patient is diagnosed with a staphylococcal infection.

3. The method of claim 1, wherein the staphylococcal infection causes at least one symptom comprising skin infection, pneumonia, bone infection, toxic shock syndrome, blood poisoning, or endocarditis.

4. The method of claim 1, wherein the method includes the step of:
identifying the patient colonized by a *staphylococcus*.

5. The method of claim 1, wherein the therapeutically effective dose of the compound according to Formula 2, is between about 0.05 mg to about 50 mg and the dose of the compound is administered to the patient once after infection.

* * * * *